United States Patent
Birkbeck

(10) Patent No.: US 9,056,826 B2
(45) Date of Patent: Jun. 16, 2015

(54) PROCESS FOR THE PREPARATION OF BETA-SANTALOL

(75) Inventor: Anthony A. Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/130,921

(22) PCT Filed: Jun. 28, 2012

(86) PCT No.: PCT/EP2012/062614
§ 371 (c)(1),
(2), (4) Date: Jan. 4, 2014

(87) PCT Pub. No.: WO2013/001026
PCT Pub. Date: Jan. 3, 2013

(65) Prior Publication Data
US 2014/0213818 A1    Jul. 31, 2014

Related U.S. Application Data

(60) Provisional application No. 61/503,224, filed on Jun. 30, 2011.

(30) Foreign Application Priority Data

Jun. 30, 2011  (EP) ..................................... 11172037

(51) Int. Cl.
| | |
|---|---|
| C07C 57/26 | (2006.01) |
| C07C 67/297 | (2006.01) |
| C07C 69/007 | (2006.01) |
| C07C 69/24 | (2006.01) |
| C07C 67/00 | (2006.01) |
| C07C 67/283 | (2006.01) |
| C07C 69/145 | (2006.01) |
| C07C 69/63 | (2006.01) |
| C07C 45/51 | (2006.01) |
| C07C 45/74 | (2006.01) |
| C07C 29/09 | (2006.01) |

(52) U.S. Cl.
CPC ............. C07C 57/26 (2013.01); C07C 67/297 (2013.01); C07C 69/007 (2013.01); C07C 69/24 (2013.01); C07C 2102/42 (2013.01); C07C 67/00 (2013.01); C07C 67/283 (2013.01); C07C 69/145 (2013.01); C07C 69/63 (2013.01); C07C 45/511 (2013.01); C07C 45/74 (2013.01); C07C 29/095 (2013.01)

(58) Field of Classification Search
CPC .... C07C 57/26; C07C 67/297; C07C 69/007; C07C 69/24
USPC ................................................. 560/265, 256
See application file for complete search history.

(56) References Cited

U.S. PATENT DOCUMENTS

| | | | |
|---|---|---|---|
| 3,662,008 A | 5/1972 | Kretschmar et al. | |
| 3,679,756 A | 7/1972 | Kretschmar et al. | |

2007/0053860 A1    3/2007   Eh et al.

FOREIGN PATENT DOCUMENTS

| | | |
|---|---|---|
| EP | 0 010 213 A2 | 4/1980 |
| EP | 2 119 714 A1 | 11/2009 |
| WO | 2005/037243 A1 | 4/2005 |
| WO | 2008/120175 A1 | 10/2008 |
| WO | 2009/141781 A1 | 11/2009 |

OTHER PUBLICATIONS

Fehr et al, Chemistry A European Journal, (2011), 17(4), p. 1257-1260. (disclosed in the IDS).*
International Search Report and Written Opinion, Application No. PCT/EP2012/062614, Aug. 3, 2012.
Alder et al., "Die Synthese der stereoisomeren Iso-santene. Darstellung des 2.3-Dimethylen-1.4-endomethylencyclohexans und seine Uberfuhrung in Santen," Chem. Ber., 88:407-419 (1955).
Brunke et al., "The Chemistry of Sandalwood Odour—A Review of the Last 10 Years," Rivista Italiana EPPOS, pp. 49-83 (1997).
Cornish et al., "Homogeneous Catalysis. IV. Hydrosilylation of Cyclic or Linear Dienes Using Low-Valent Nickel Complexes and Related Experiments," Journal of Organometallic Chemistry, 132:133-148 (1977).
Ely et al., "Regio-and Stereoselective Ni-Catalyzed 1,4-Hydroboration of 1,3-Dienes: Access to Stereodefined (Z)-Allylboron Reagents and Derived Allylic Alcohols," J. Am. Chem. Soc., 132:2534-2535 (2010).
Fehr et al., "Enantioselective Synthesis of (–)-β-Santalol by a Copper-Catalyzed Enynol Cyclization-Fragmentation Reaction," Angew. Chem. Int. Ed., 48:7221-7223 (2009).
Fehr et al., "The Synthesis of (Z)-Trisubstituted Allylic Alcohols by the Selective 1,4-Hydrogenation of Dienol Esters: Improved Synthesis of (–)-β-Santalol," Chem. Eur. J., 17:1257-1260 (2011).
Han et al., "Diastereo- and Enantioselective anti-Alkoxyallylation Employing Allylic gem-Dicarboxylates as Allyl Donors via Iridium-Catalyzed Transfer Hydrogenation," J. Am. Chem. Soc., 132:1760-1761 (2010).
Herberich et al., "3-Borolene mit diastereotopen Seiten: Synthese von 4-(Dialkylamino)-4-boratri-cyclo[5.2.1.0 2,6] dec-2(6)-enen und Struktur des Dimethylamino-Derivats," Chem. Ber., 127:1401-1404 (1994).

(Continued)

Primary Examiner — Yong Chu
(74) Attorney, Agent, or Firm — Winston & Strawn LLP

(57) ABSTRACT

The present invention concerns a process for the preparation of a compound of formula (I) in the form of any one of its stereoisomers or mixtures thereof, and wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms. The invention concerns also the use of compound (I) for the synthesis of β-santalol or of derivatives thereof.

(I)

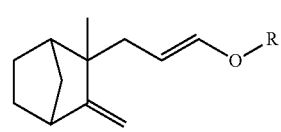

12 Claims, No Drawings

(56) References Cited

OTHER PUBLICATIONS

Herberich et al., "Synthese von-C-substituierten 2,5-Dihydro-1H-borolen (3-Borolenen)," Chem. Ber. 127:2135-2140 (1994).

Kretschmar et al., "The Isolation and Synthesis of a Novel Tetracyclic Ether from East Indian Sandalwood Oil. A Facile Intromolecular Prins Reaction," Tetrahedron Letters, 1:37-40 (1970).

Krotz et al., "Total Syntheses of Sandalwood Fragrances: (Z)- and (E)-β-Santalol and Their Enantiomers, ent-β-Santalene," Tetrahedron: Asymmetry, 1(8):537-540 (1990).

Neuenschwander et al., "Chloracylierung und Bromacylierung von Carbonylverbindungen: Eine in Vergessenheit geratene Carbonylreaktion. I. Präparative Anwendungsbreite," Helvetica Chimica Acta, 61(6):2047-2058 (1978).

Pock et al., "Elektrophile Alkylierungen von Norbornen—Synthese 7-substituierter Norbornene," Chem. Ber., 119:929-942 (1986).

Simmons et al., "Aldehyde Enol Esters as Novel Chain Terminators in Cationic Olefin Cyclizations," Helvetica Chimica Acta, 71:1000-1004 (1988).

Takahashi et al., "A New Method for the Introduction of Carbon-Carbon Triple Bond at C-13 in PG Synthesis. A Stereocontrolled Synthesis of K96 480," J. Org. Chem., 53:1227-1231 (1988).

Trost et al., "Geminal Dicarboxylates as Carbonyl Surrogates for Asymmetric Synthesis. Part I. Asymmetric Addition of Malonate Nucleophiles," J. Am. Chem. Soc., 123:3671-3686 (2001).

Wu et al., "Iron-Catalyzed 1,4-Hydroboration of 1,3-Dienes," J. Am. Chem. Soc., 131:12915-12917 (2009).

Wu et al., "A Strategy for the Synthesis of Well-Defined Iron Catalysts and Application to Regioselective Diene Hydrosilylation," J. Am. Chem. Soc., 132:13214-13216 (2010).

\* cited by examiner

PROCESS FOR THE PREPARATION OF BETA-SANTALOL

TECHNICAL FIELD

The present invention relates to the field of organic synthesis and more specifically it concerns a process for the preparation of a compound of formula

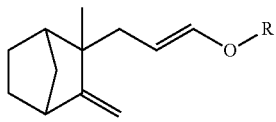
(I)

wherein R is as defined below, and said compound is in the form of any one of its stereoisomers or mixtures thereof. The invention also concerns the use of compound (I) for the synthesis of β-santalol or of derivatives thereof.

PRIOR ART

The compounds of formula (I) are useful starting materials for the preparation of β-santalol ((Z)-2-methyl-5-((1SR,2RS,4RS)-2-methyl-3-methylenebicyclo[2.2.1]heptan-2-yl)pent-2-en-1-ol, i.e. the exo isomer), and derivatives thereof, in a short, effective and industrially feasible manner. Said compounds (I) are also novel.

The β-santalol, and derivatives thereof, are well known and highly valued perfuming ingredients, some of which have particular relevance. Synthetic β-santalol is not commercially available at this time and it is only available from natural sources (Sandalwood sp. essential oils). β-santalol is present in East Indian Sandalwood Oil (*Santalum album*) at a typical level of 20-25% and is generally accepted as the principal odour vector for the fine creamy sandalwood character of the essential oil. The West Australian Sandalwood Oil (*Santalum spicatum.*) typically contains much less β-santalol, in the range of 3-8% of the essential oil, and as a result is a less appreciated oil.

The export of East Indian sandalwood and the distillation of the essential oil is under strict government control since *Santalum album* has been classified by the Convention on International Trade in Endangered Species of Wild Fauna and Flora and International Union for Conservation of Nature Red list as vulnerable and at risk of extinction.

Therefore, there is an urgent need for alternative syntheses to produce β-santalol and its derviatives.

To the best of our knowledge, all known syntheses are lengthy, require expensive starting materials and/or reagents or even steps which are too expensive for an industrial process or generate unacceptable quantities of waste (e.g. see Brunke at al., in Rivista Italiana EPPOS, 1997, 49). In particular one may cite the following references, which are representative of the best examples of processes for the preparation of β-santalol:

- EP 10213: however said process, besides the fact that it is very long, requires many chlorinated intermediates (not optimal for a use in perfumery) and provides a very low overall yield (about 13%) for the preparation of the aldehyde (IV) of the present invention (see below);
- A. Krotz et al., in *Tet. Asymm.*, 1990, 1, 537: describes a relatively short synthesis, however it requires expensive reducing reagents that are difficult to manipulate on large scale, expensive chiral auxiliaries, two Wittig reactions, and then the subsequent transformation of a ketone into the exo-methylene group:
- U.S. Pat. No. 3,662,008 and U.S. Pat. No. 3,679,756 also describe the synthesis of β-santalol in low overall yield. This route is similarly dependent on a Wittig reaction to install the Z double bond and expensive reducing agents;
- C. Fehr et al. in *Chem. Eur. J.* 2010, 17, 1257 or in *Angew. Chem. Int. Ed,* 2009, 48, 7221: describes a synthesis of β-santalol via the Cu catalyzed rearrangement of a propargyl alcohol derivative which is not easy to prepare on industrial scale;
- EP 2119714: describes a synthesis utilizing a 'Scriabine' reaction on an electron rich aromatic ring, but nothing about the use of such a reaction on an alkene or in the preparation of β-santalol;
- H. Mayr et al in *Chem. Ber.* 1986, 119, 929: describes a 1,4 electrophillic addition to a cyclic alkene but does not mention or suggest the preparation of β-santalol.

The aim of the present invention is to provide a more industrial and efficient process for the preparation of β-santalol, and derivatives thereof. Indeed, the present invention shortens the overall process of preparation of the targeted compounds by allowing the one-step creation of a suitably functionalised side-chain moiety (with the correct configuration) together with the concomitant formation of the methylene function (without the mandatory need of a Wittig olefination or similar transformations) using a novel reaction without literature precedent.

DESCRIPTION OF THE INVENTION

A first object of the present invention is a process for the preparation of a compound of formula

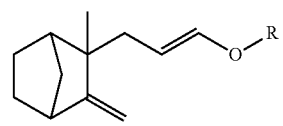
(I)

in the form of any one of its stereoisomers or mixtures thereof, wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms.

As will be further shown below, said compounds (I) are useful intermediates in the preparation of β-santalol (in particular (Z)-2-methyl-5-((1S,2R,4R)-2-methyl-3-methylenebicyclo[2.2.1]heptan-2-yl)pent-2-en-1-ol), via the preparation of 3-((1SR,2RS,4R5)-2-methyl-3-methylenebicyclo[2.2.1]heptan-2-yl)propanal (see EP 10213).

A particular aspect of the first object of the present invention is a process for the preparation of a compound of formula

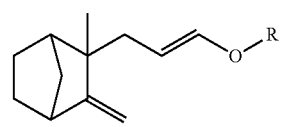
(I)

in the form of any one of its stereoisomers or mixtures thereof, and wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms;
by reacting together a compound of formula

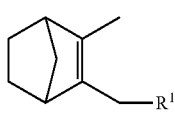
(II)

in the form of any one of its stereoisomers or mixtures thereof, and wherein $R^1$ represents a hydrogen atom or a $Si(R^2)_3$ or $B(OR^{2'})_2$ group, $R^2$ representing a $C_{1-4}$ alkyl or alkoxyl group and $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups;
with a compound of formula

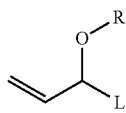
(III)

in the form of any one of its stereoisomers or mixtures thereof, and wherein R has the meaning defined in formula (I) and L represents a halogen atom or an OR group;
in the presence of
1) at least one Lewis acid selected amongst:
   i) a metal salt of a an element of the group 2, 3, 4, 13 or of a 3d element or of tin;
   ii) an alkyl aluminum chloride of formula $Al(R^4)_aCl_{3-a}$, a representing 1 or 2 and $R^4$ representing $C_{1-10}$ alkyl or alkoxide group; and
   iii) a boron derivative of formula $BZ_3$, wherein Z represents a fluoride or a phenyl group optionally substituted by one or two methyl groups, and any one of its adducts with a $C_2$-$C_{10}$ ether or a $C_1$-$C_8$ carboxylic acid; and
2) optionally an additive selected amongst the group consisting of alkaline-earth hydroxide or oxide and of the compounds of formula $R^bCOCl$, $ClSi(R^b)_3$, $R^bCOOR^c$ or $(R^bCOO)_2R^d$, $R^b$ representing a $C_{1-12}$ alkyl group or a phenyl group optionally substituted by one or two $C_{1-4}$ alkyl or alkoxyl group, and $R^c$ representing a alkaline metal cation or a $R^bCO$ acyl group, and $R^d$ representing a alkaline-earth metal cation.

For the sake of clarity, by the expression "group 2, 3, 4, 13" it is understood the usual meaning in the art and it is made reference to the periodic table classification (e.g. see http://en.wikipedia.org/wiki/Periodic_table) Similarly by the expression "3d metal" it understood a chemical element having an atomic number comprised between 21 and 30 included.

The invention process is, to the best of our knowledge, the first example of a Scriabine type reaction reported in the literature using an alkene instead of an aromatic compound.

The compound of formula (II) can be obtained according to *Chem. Ber.*, 1955, 88, 407 (for santene, i.e. $R^1$ is a hydrogen atom).

The corresponding silyl ($R^1$=$Si(R^2)_3$) or boryl ($R^1$=$B(OR^{2'})_2$) compounds can be obtained by either 1,4 hydrosilylation, (see *J. Organometallic Chem.*, 1977, 132, 133, *J. Am. Chem. Soc.*, 2010, 132, 13214) or 1,4 hydroboration (see *J. Am. Chem. Soc.*, 2009, 131, 12915, or *J. Am. Chem. Soc.*, 2010, 132, 2534.) of the corresponding santadiene (see *Chem. Ber.*, 1955, 88, 407). Alternatively these same products can be obtained via mono functionalisation of santene via deprotonation with Lochmann-Schlosser base as described in *Chem Ber.*, 1994, 127, 1401 and *Chem. Ber.*, 1994, 127, 2135 using the appropriate reagent.

According to any embodiment of the invention, and independently of the specific aspects, said $R^1$ group represent a hydrogen atom.

Alternatively said $R^1$ group represents a $Si(R^2)_3$, $R^2$ representing a $C_{1-4}$ alkyl or alkoxyl group, or a $B(OR^{2'})_2$ group, $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups.

According to any embodiment of the invention, said compound (II) is triethyl (((1SR,4RS)-3-methylbicyclo[2.2.1]hept-2-en-2-yl)methyl)silane, 2,3-dimethylbicyclo[2.2.1]hept-2-ene (santene) or 4,4,5,5-tetramethyl-2-(1SR,4RS)-3-methylbicyclo[2.2.1]hept-2-en-2-yl)methyl)-1,3,2-dioxaborolane. In particular, said compound (II) is 2,3-dimethylbicyclo[2.2.1]hept-2-ene (santene).

The compound of formula (III) can be obtained according to *J. Am. Chem. Soc.*, 2001, 123, 3671; or for the chloro derivative following *Bull. Soc. Chim. de France*, 1938, 5, 256 or according to *Helv. Chim. Acta.*, 1978, 61, 2047.

Furthermore, a second object of the invention is the novel and useful compounds of formula (I)

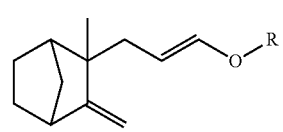
(I)

in the form of any one of its stereoisomers or mixtures thereof, and wherein R has the meaning indicated above in formula (I). In particular one may cite the (E)-3-((1SR,2RS,4RS)-2-methyl-3-methylenebicyclo[2.2.1]heptan-2-yl)prop-1-en-1-yl carboxylates, wherein by carboxylate it is meant a $C_{1-7}$, preferably a $C_{2-6}$, acyl group as defined above.

According to any embodiment of the invention, and independently of the specific aspects, said R group represents a $C_2$-$C_{10}$ group of formula $COR^a$ wherein $R^a$ is an alkyl or alkenyl group optionally comprising one or two ether functional groups or represents a phenyl or benzyl group optionally substituted by one or two $C_{1-2}$ alkyl, alkoxyl, carboxyl, acyl, amino or nitro groups or halogen atoms.

According to any embodiment of the invention, and independently of the specific aspects, said R group represents an acyl group of formula $COR^a$ wherein, and $R^a$ is
  a phenyl or benzyl group optionally substituted by one or two $C_{1-2}$ alkyl, alkoxyl, carboxyl, acyl, amino or nitro groups; or
  a $C_3$-$C_9$ branched alkyl or alkenyl group comprising in the α position a tertiary or quaternary carbon atom and/or in the β position a quaternary carbon atom.

According to any embodiment of the invention, said R is a $C_2$-$C_5$ acyl group. In particular said R group is an acyl group $R^aCO$ and $R^a$ is a branched alkyl group comprising in the α position a tertiary or quaternary carbon atom and/or in the β position a quaternary carbon atom.

For the sake of clarity, by the expression "α position" it is meant the usual meaning in the art, i.e. the carbon atom directly bound to the COO moiety of the group R. Similarly by the expression "β position" it is meant a carbon atom directly bound to the α position.

Specific examples of said R are, EtCO, $^i$PrCO, $^{sec}$BuCO, $^t$BuCH$_2$CO, $^t$BuCO PhCO or PhCH$_2$CO.

According to any embodiment of the invention, and independently of the specific aspects, said L group represent a Cl atom or represents a OR group as defined above.

The process for the preparation of a compound (I), according to the invention, requires a Lewis acid, which is used as catalyst for the Scriabine type reaction.

The invention process is carried out in the presence of a Lewis acid of various types, inter alia a particular metal salt. According to any embodiment of the invention, and independently of the specific aspects, said metal salt is advantageously selected amongst the compounds formula

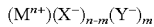

wherein m is an integer from 0 to (n−1), and
n is 2 and M is Zn, Cu or an alkaline earth metal;
n is 3 and M is a lanthanide, Sc, Fe, Al; or
n is 4 and M is Sn, Ti or Zr;
each $X^-$ represents $Cl^-$, $Br^-$, $I^-$, a weakly-coordinating monoanion, $R^3SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups;
each $Y^-$ represents a $C_{1-6}$ carboxylate or 1,3-diketonate when n is 2 or 3, or a $C_{1-6}$ alkoxylate when n is 3 or 4.

By the expression "weakly-coordinating monoanion" it is meant the usual meaning in the art, i.e. an monoanion which is non-coordinated or very weakly coordinated to the metal center. Typically such weakly-coordinating monoanions are the anions of acids HX having a $pK_a$ below 1. Non limiting examples of such non-coordinating monoanions are $ClO_{4-}$, $BF_{4-}$, $PF_6^-$, $SbCl_6^-$, $AsCl_6^-$, $SbF_6^-$, $AsF_6^-$ or $BR_{4-}$, wherein R is a phenyl group optionally substituted by one to five groups such as halide atoms or methyl or $CF_3$ groups, and in particular are $PF_6^-$ or $BF_4^-$.

According to any embodiment of the invention, and independently of the specific aspects, said metal salt is advantageously selected amongst the compounds formula

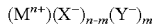

wherein m is an integer from 0 to (n−1), and
n is 2 and M is Zn or Cu;
n is 3 and M is Ce, Sc, Al; or
n is 4 and M is Ti or Zr;
each $X^-$ represents CY, $Br^-$, $I^-$, $PF_6^-$, $BF_4^-$, $R^3SO_3^-$ wherein $R^3$ represents a chlorine or fluorine atom, or a $C_{1-3}$ hydrocarbon or perfluoro hydrocarbon;
each $Y^-$ represents a $C_{1-6}$ carboxylate or 1,3-diketonate when n is 2 or 3, or a $C_{1-6}$ alkoxylate when n is 3 or 4.

According to any embodiment of the invention, said $X^-$ represents $Cl^-$, $Br^-$, $I^-$, $CF_3SO_3^-$ or $BF_4^-$.

According to any embodiment of the invention, when n is 2 $X^-$ represents a $Cl^-$, $Br^-$, $I^-$, $CF_3SO_3^-$ or $BF_4^-$, or when n is 3 $X^-$ represents a $Cl^-$, $CF_3SO_3^-$ or $BF_4^-$, or n is 4 $X^-$ represents a $Cl^-$. It is understood by a person skilled in the art that the nature of X may depend on the redox potential of the anions X (in particular when said anion X is an halogen) and the redox potential of the metal cation.

According to any embodiment of the invention, said $Y^-$ represents a $C_{1-6}$ carboxylate when n is 2 or 3, or a $C_{1-3}$ alkoxylate when n is 3 or 4.

According to any embodiment of the invention, and independently of the specific aspects, said metal salt is selected amongst a salt of formula

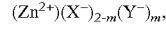

wherein m, $X^-$ and $Y^-$ have the meaning indicated above, in particular m is 0;

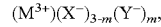

wherein m, $X^-$ and $Y^-$ have the meaning indicated above and M is Al or Sc, in particular m is 0, 1 or 2;

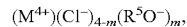

wherein m has the meaning indicated above, M representing Ti or Zr, and $R^5$ representing $C_{1-3}$ alkyl group, in particular m is 1, 2 or 3.

According to any embodiment of the invention, said metal salt is a salt of formula:

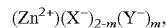

wherein m, $X^-$ and $Y^-$ have the meaning indicated above;

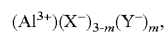

wherein m, $X^-$ and $Y^-$ have the meaning indicated above;

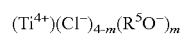

wherein m has the meaning indicated above, and $R^5$ representing $C_{1-3}$ alkyl group.

According to any embodiment of the invention, and independently of the specific aspects, said metal salt is one wherein n is 2 or 3.

The metal salt can be added to the reaction medium as a preformed salt or generated in situ, for example as described in the Examples e.g. by the reaction of a carboxylate salt (for example $Zn(AcO)_2$) with $ClSi(R^b)_3$ or $R^bCOCl$.

Said Lewis acid may be also an alkyl aluminum chloride. According to any embodiment of the invention, and independently of the specific aspects, said alkyl aluminum chloride is of formula $Al(R^4)_aCl_{3-a}$, a representing 1 or 2 and $R^4$ representing $C_{1-4}$ alkyl or alkoxide group. According to any embodiment of the invention, and independently of the specific aspects, said alkyl aluminum chloride is selected amongst the compounds of formula $Al(R^4)_aCl_{3-a}$, a representing 1 or 2 and $R^4$ representing a $C_{1-3}$ alkyl group. According to any embodiment of the invention, said alkyl aluminum chloride is a compound wherein 'a' represents 1 and $R^4$ represents a $C_{1-3}$ alkyl group, such as $EtAlCl_2$ or $MeAlCl_2$.

Said Lewis acid may be also a boron derivative of formula $BZ_3$. According to any embodiment of the invention, and independently of the specific aspects, said boron derivative is of formula $BZ_3$, wherein Z represents a fluoride or a phenyl group optionally substituted, and any one of its adduct with a $C_2$-$C_8$ ether or a $C_1$-$C_6$ carboxylic acid. According to any embodiment of the invention, and independently of the specific aspects, said boron derivative is $BF_3$, and any one of its adduct with a $C_4$-$C_6$ ether or a $C_1$-$C_3$ carboxylic acid, such as $BF_3$ $(EtOEt)_{1-2}$ or $BF_3$ $(AcOH)_{1-2}$.

According to any embodiment of the invention, said Lewis acid is selected amongst $EtAlCl_2$, $MeAlCl_2$ or $(Zn^{2+})(X^-)_2$, $X^-$ being as defined above and in particular $Br^-$, $I^-$ or $Cl^-$.

Optionally, to said process of the invention, it can be also added, an additive. Said additive accelerate the reaction and/or provide better yield of the desired product. According to any one of the above embodiments of the invention, said additive is amongst the group consisting of the compounds of formula $R^bCOCl$, $ClSiR^b_3$, $R^bCOOR^c$ or $(R^bCOO)_2R^d$, $R^b$ representing a $C_{1-8}$, or even $C_{1-4}$, alkyl group or a phenyl group optionally substituted by one or two $C_{1-4}$ alkyl or alkoxyl group, and $R^c$ representing a Li, Na, or K cation or a $R^bCO$ acyl group, and $R^d$ representing a Mg or Ca cation.

According to any one of the above embodiments of the invention, said additive, as non limiting example, can be $ClSiMe_3$, MeCOCl, AcOK or AcOAc.

In particular, when the Lewis acid is a metal salt as above defined then it is most advantageous to use an additive of the silyl or acyl chloride type. Similarly, when the Lewis acid is of the alkyl aluminum chloride type or a boron derivative as above described then it is most advantageous to use an additive of the alkali carboxylate or of the carboxylic anhydride type.

It goes without saying, as a person skilled in the art knows, that the addition of said additive, can be done in one-pot (e.g. together with the catalyst or subsequently to the catalyst, in the same reaction medium) or in a kind of a two pot process (e.g. treating compounds (II) and (III) together with the catalyst and after a purification of the product thus obtained performing a treatment of said compound with the additive in a different reaction medium).

This second option (two-pot treatment) is particularly interesting in the case the Lewis acid is an alkyl aluminum chloride, since surprisingly we found that, in addition to the desired compound (I), an important product of the treatment with the Lewis acid can be a compound of formula

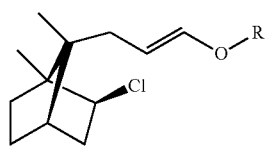

(I″)

in the form of any one of its stereoisomers or mixture thereof, and wherein R has the same meaning as defined above; and that said compound (I″) can be converted into the desired product (I), by adding an additive such as an alkali or alkaline-earth carboxylate or a carboxylic anhydride, preferably an alkali carboxylate, as defined for the additive. Said compound (I″) is novel, and therefore as intermediate of compound (I) is also another aspect of the present invention.

The Lewis acid can be added to the reaction medium in a large range of concentrations. As non-limiting examples, one can cite a boron derivative or a transition metal salt, as described above, concentrations ranging from about 0.01 to 0.30 molar equivalents, relative to the molar amount of the starting compound (III), preferably comprised between about 0.03 and 0.15 molar equivalents. As non-limiting examples, one can cite alkyl aluminum chloride, as described above, concentrations ranging from about 0.5 to 2.00 molar equivalents, relative to the molar amount of the starting compound (III), preferably comprised between about 0.7 and 1.3 molar equivalents.

It goes without saying that the optimum concentration of the salt will depend on the nature of the latter and on the desired reaction time, as well as the presence of an additive or not.

The additive can be added to the reaction medium in a large range of concentrations. As non-limiting examples, one can cite additive concentrations ranging from 10 to 250%, relative to the weight of the Lewis acid. Preferably, the additive concentration will be comprised between 10 and 120%, relative to the weight of the Lewis acid.

The process for the preparation of a compound (I), according to the invention, can be carried out under a number of various reaction conditions, provided that they are compatible with the reagents and the reactivity of the salt and additive. A person skilled in the art is able to select the most appropriate ones in view of its own needs. According to any embodiment of the invention, and independently of the specific aspects, one may cite as non limiting examples the following conditions, independent from each other or associated in any combination:

- a reaction temperature comprised between −78° C. and 150° C., preferably between 0° C. and 70° C.; of course a person skilled in the art is also able to select the preferred temperature as a function of the melting and boiling point of the starting and final products and/or an eventual solvent;
- the transformation of (II) into (I), in any of its embodiments, can be carried out in absence or in the presence of solvent; non-limiting examples of such a solvent are $C_{2-10}$ saturated esters, $C_{1-6}$ saturated chlorinated solvents, $C_{6-9}$ saturated or aromatic hydrocarbons (the latter are surprising since we observed no competition in the Scriabine type reaction with the starting compound (II)) and mixtures thereof. More preferably, the solvent is 1,2-dichloroethane, dichloromethane, chlorobenzene, dichlorobenzenes, toluene or xylene.

Another object of the invention, is a process for the preparation of a compound of formula

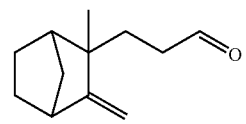

(IV)

in the form of any one of its stereoisomers or mixture thereof; characterized in that a compound of formula (I) as defined above is reacted with a $C_{4-12}$ tertiary amine in an alcoholic solvent.

Typical, and non limiting examples of said tertiary amine, used to perform a non acidic trans-esterification is 4-dimethyl-pyridine, triethylamine, $EtNMe_2$, N-methyl-piperidine, diazabicyclo[2.2.2]octane, N-methyl-pyrolidine or 4-(pyrrolidin-1-yl)pyridine. Preferably said tertiary amine is an aromatic or saturated $C_{6-10}$ cyclic tertiary amine.

The advantage of these non-acidic conditions, allowed by the invention process and intermediate (I'), is to avoid or minimize the transformation of aldehyde (IV) into tetracyclic ether (described in Tet. Lett., 1970, 11, 37).

The experimental conditions of said process are quite standard for such type of reaction. However, independently of the specific aspects, one may cite as non limiting examples the following conditions, independent from each other or associated in any combination:

- the tertiary amine can be added to the reaction medium in a large range of concentrations, such as concentrations ranging from 0.01 to 5 molar equivalents, relative to the amount of the compound (I');
- a reaction temperature comprised between 0° C. and 175° C., preferably between 40° C. and 70° C.; of course a person skilled in the art is also able to select the preferred temperature as a function of the melting and boiling point of the starting and final products and/or an eventual solvent;

the alcoholic solvent of the reaction can be a $C_{1-6}$, or $C_{1-4}$, alcohol and its mixtures with $C_{2-10}$, or $C_{2-6}$, esters, $C_{6-10}$ aromatic hydrocarbons or $C_{1-6}$, or $C_{1-2}$, chlorinated solvents More preferably, the solvent is a primary alcohol such as methanol or ethanol.

According to any embodiment of the invention, and independently of the specific aspects, the compounds (I), (I"), (II) or (IV) can be in the form of any one of its stereoisomers or mixtures thereof. For the sake of clarity by the term stereoisomer it is intended any diastereomer, enantiomer, racemate or carbon-carbon double bond isomer of configuration E or Z.

According to any embodiment of the invention, compound (I) is in the form of a mixture of stereoisomers comprising more than 50% (w/w) of the (1SR,2RS,4RS) stereoisomer, i.e. a compound having the relative exo (the bridging carbon atom and the enol chain being in a relative cis configuration) configuration as shown in formula (I-A)

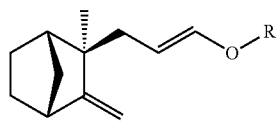

(I-A)

wherein R has the meaning indicated above in formula (I), and the bold and hatched lines indicate a relative configuration.

According to any embodiment of the invention, compound (I) is in the form of a mixture of stereoisomers comprising more than 50% (w/w) of the (1S,2R,4R) stereoisomer, i.e. a compound having the absolute configuration as shown in formula (I-B)

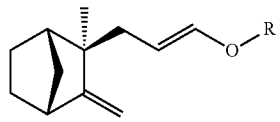

(I-B)

wherein R has the meaning indicated above in formula (I), and the bold and hatched lines indicate an absolute configuration.

It is understood that, in any of the above or below embodiments, the starting material to prepare (e.g. (II) and (I")) or the product obtained from (e.g. see below (IV), (V), (VI), (VII) and β-santalol) said compound (I) may have, and preferably does have, the same stereo configuration, i.e, if it is used the exo-(I) then all compounds (V), (VI), (VII) and β-santalol will have the exo configuration. By way of examples one may cite the following reaction scheme:

Scheme 1:

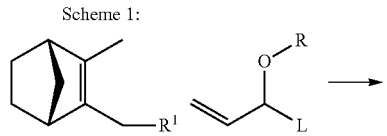

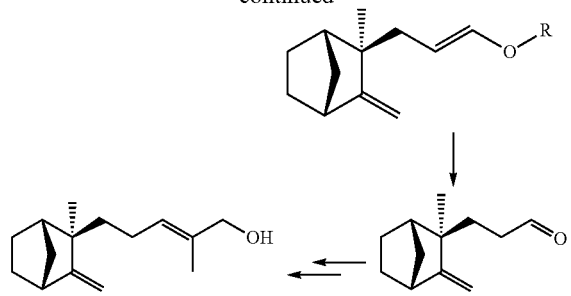

the stereo configuration being relative or absolute.

A further object of the present invention is a process for the preparation of β-santalol, or its derivatives such as β-santalal, β-santalyl benzoate, β-santalyl butyrate, β-santalyl isobutyrate, β-santalyl propionate, comprising a step as defined above. It is understood that a person skilled in the art know how to perform said process using compound (I) obtained according to the invention's process.

The transformation of the aldehyde (IV) into β-santalol can be performed in many different ways, which are well known to a person skilled in the art. Practical examples are provided in Examples herein below.

However, as a non-limiting example, one of the most direct manners to transform the aldehyde (IV) into β-santalol comprises of the following reactions:

a) coupling said aldehyde (IV) with an aldehyde $CH_3CH_2CHO$ (Aldol addition) to obtain an aldehyde (V)

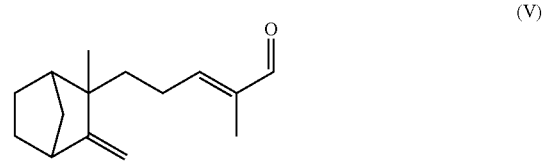 [SMILES: C=C1C2CCC(C2)C1(C)CC/C=C(\C)C=O]

(V)

in the form of any one of its stereoisomers or mixtures thereof;

b) converting said compound (V) into the corresponding dienol derivative (VI)

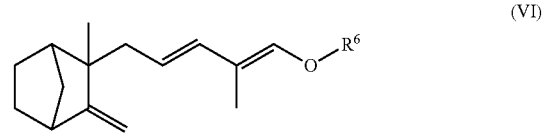

(VI)

in the form of any one of its stereoisomers or mixtures thereof, and $R^6$ represents a $C_1$-$C_6$ alkyl, alkenyl or acyl group or a $C_3$-$C_9$ silyl group;

c) reducing the dienol derivative (VI) into a compound (VII)

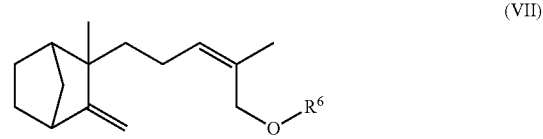

(VII)

in the form of any one of its stereoisomers or mixtures thereof, and wherein $R^6$ has the same meaning as in formula (VI);

d) converting said compound (VII) into the β-santalol.

According to a particular embodiment of the invention, said compounds (IV) to (VI) possess a configuration corresponding to the one described above for compounds (I-A) or (I-B).

Steps a) to d) can be performed according to standard methods well known by a person skilled in the art.

For instance, one may cite the following method for each step:

step a) according to EP 10213;

step b) according to Simmons et al. in *Helv. Chim. Acta,* 1988, 71, 1000, or WO 2005/037243; and step c) according to Shibasaki et al., in *J. Org. Chem.,* 1988, 53, 1227 (where is reported the [1,4] hydrogenation of a dienol acetate derivative) or according to WO 08/120175 or WO 09/141781; and step d): see WO 09/141781.

An example of such a procedure is provided in the Examples herein below.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 400 MHz or 125 MHz machine for $^1H$ or $^{13}C$ respectively, the chemical shifts δ are indicated in ppm with respect to TMS as standard, the coupling constants J are expressed in Hz. Chromatography was performed using Analogix Cartridges containing silica with specified solvent mixtures under pressure. Santene (2,3-dimethylbicyclo[2.2.1]hept-2-ene) was prepared according to *Chem. Ber.,* 1955, 88, 407.

Various compounds of formula (III) were prepared following the general procedure: herein below:

$FeCl_3.6H_2O$ (100 mg, cat.) was added to a stirred solution of acrolein (5.6 g, 100 mmol) in dichloromethane (25 ml) then cooled to 0° C. The suitable carboxylic anhydride (100 mmol) was added slowly dropwise. After 2 hours at 0° C. the solution was stirred for a further 30 minutes at ambient temperature then poured into saturated $NaHCO_3$ and ethyl acetate (100 ml), re-extracted with ethyl acetate, and the combined organic phases were washed with $NaHCO_3$, then dried over $MgSO_4$, filtered and the solvents removed in vacuo to yield the crude allylidene diesters. Further purification by bulb to bulb distillation gave the desired diesters.

prop-2-ene-1,1-diyl diacetate see *J. Am. Chem. Soc.,* 2001, 123, 3671 prop-2-ene-1,1-diyl dipropionate

Bulb to bulb distillation at 130° C. at 10 mbar gave the dipropionate, 10 g, yield=53%.

$^{13}C$ NMR: 172.2 (s), 131.5 (d), 120.3 (t), 89.0 (d), 27.4 (t), 8.7 (q).

prop-2-ene-1,1-diyl diisobutyrate

Bulb to bulb distillation at 90-100° C. at 0.45 mbar gave the allylidene disobutyrate, 12.8 g, yield=59%.

$^{13}C$ NMR: 174.8 (s), 131.5 (d), 120.2 (t), 89.0 (d), 33.9 (d), 18.7, 18.6 (q).

prop-2-ene-1,1-diyl dipivalate

Bulb to bulb distillation at 110° C. at 0.56 mbar gave the dipivalate, 13.87 g, yield=57%.

$^{13}C$ NMR: 176.2 (s), 131.6 (d), 119.9 (t), 88.9 (d), 38.8 (s), 26.8 (q) ppm.

Example 1

Preparation of (E)-3-((1SR,2RS,4RS)-2-methyl-3-methylenebicyclo[2.2.1]heptan-2-yl)prop-1-en-1-yl acetate, and corresponding compounds (I″) (E)-3-((1SR,2RS,4RS)-2-chloro-1,7-dimethylbicyclo[2.2.1]heptan-7-yl)prop-1-en-1-yl acetate Procedure 1: Use of $EtAlCl_2$ Allylidene diacetate (15.8 g, 100 mmol, 2 equivalents) was dissolved in dichloromethane (50 ml) and cooled to about 2° C. Then a solution of $EtAlCl_2$ (80 ml, 1.0 M in hexane, 80 mmol) was added slowly dropwise over 20 minutes. Santene (6.1 g, 50 mmol) was then added dropwise. The reaction mixture was allowed to slowly warm to ambient temperature. Left to stir at ambient temperature for a further 3 hours and then diluted with ethyl acetate, then was poured into saturated $NaHCO_3$, re-extracted with ethyl acetate, and the combined organic phases washed with saturated $NH_4Cl$, dried over $MgSO_4$, filtered and the solvents removed in vacuo to yield the crude enol acetates, 15.6 g as a pale yellow oil. Distillation at 0.45 mbar 150-200° C. gave a mixture of the enol acetate (I) and chloro compound (I″) (ratio: 17:37).

Said crude was either:

dissolved in acetic anhydride (5 g) and potassium acetate (2.5 g) was added. The suspension was heated under reflux for 45 minutes. Then cooled and poured into saturated $NaHCO_3$, stirred overnight. The reaction medium was extracted with ethyl acetate, and the combined organic extract washed with $NaHCO_3$ then dried over $MgSO_4$, filtered and the solvents was removed in vacuo to yield 5.4 g of the crude enol acetate. Bulb to bulb distillation 120-140° C. at 0.7 mbar, gave the enol acetate 4.16 g. Chromatography with cartridge (150 g) with cyclohexane then 1:99 ethyl acetate:cyclohexane as eluent gave the pure enol acetate, 4.25 g, yield=38% (exo:endo 6:1); or purified by a bulb to bulb distillation 120-140° C. at 0.46 mbar. It was obtained a mixture of the chloro enol acetate (I″) and the enol acetate (I) (ratio of 17:54). Re purified by flash chromatography cartridge 80 g with cyclohexane then 98:2 cyclohexane:ethyl acetate as eluent gave the desired enol acetate, 0.65 g (exo:endo 6:1) and the chloro compound, 0.2 g.

(E)-3-((1SR,2RS,4RS)-2-methyl-3-methylenebicyclo[2.2.1]heptan-2-yl)prop-1-en-1-yl acetate $^{13}C$ NMR: 168.2 (C), 165.1 (C), 136.6 (CH), 111.7 (CH), 100.2 ($CH_2$), 46.8 (CH), 44.8 (CH), 44.7 (C), 38.6 ($CH_2$), 37.0 ($CH_2$), 29.6 ($CH_2$), 23.6 ($CH_2$), 22.8 ($CH_3$), 20.7 ($CH_3$).

(E)-3-((1SR,2RS,4RS)-2-chloro-1,7-dimethylbicyclo[2.2.1]heptan-7-yl)prop-1-en-1-yl acetate $^{13}C$ NMR: 168.1 (C), 136.2 (CH), 112.2 (CH), 68.0 (CH), 50.5 (C), 50.4 (C), 43.3 (CH), 42.1 ($CH_2$), 36.8 ($CH_2$), 30.6 ($CH_2$), 26.7 ($CH_2$), 20.7 ($CH_3$), 16.7 ($CH_3$), 13.5 ($CH_3$).

Procedure 2: Use of EtAlCl₂

Allylidene diacetate (15.8 g, 100 mmol, 2 equivalents) was dissolved in dichloromethane (50 ml) then cooled to 2° C. in an ice bath. EtAlCl₂ (1.0 M in hexanes, 50 ml, 50 mmol) was added slowly dropwise over 15 minutes. Santene (6.1 g, 50 mmol) was then added slowly dropwise and the mixture allowed to slowly warm to 25° C. in ice bath over 2 hours. Cooled to 3° C. and then there was added a further portion of catalyst (25 ml, 1.0 M, 25 mmol) slowly dropwise. After 6 hours at ambient temperature the reaction mixture was poured into a mixture of cyclohexane (100 ml), ethyl acetate (100 ml) and potassium acetate (20% aqueous, 200 ml) and all was stirred overnight. Then the medium was extracted with ethyl acetate, and the combined organic phases washed with NH₄Cl, then NaHCO₃, dried over MgSO₄, filtered and the solvents removed in vacuo to yield the crude enol acetates. Potassium acetate (8.0 g) was added followed by acetic anhydride (10 g) and the suspension heated at reflux for 45 minutes, then cooled. Poured into ethyl acetate, then washed with NaHCO₃, dried over MgSO₄, filtered and the solvents removed in vacuo. Azeotropic removal of acetic anhydride with toluene gave the crude enol acetate 15.8 g. Added Potassium acetate (1.0 g) as stabilizer then bulb to bulb distillation 0.65 mbar, at 150° C. gave the desired enol acetate, 5.3 g, yield=48% (NMR identical to that prepared above) (exo: endo=6:1).

Procedure 3: Use of ZnCl₂ (Generated In Situ by Powder Zn and Trimethyl Silyl Chloride)

Zn powder (65 mg, 1 mmol) was added to a stirred solution of trimethyl silyl chloride (1.03 g, 9.5 mmol) stirred for 30 minutes and then allylidene diacetate (6.3 g, 40 mmol) was added and the suspension stirred for a further 15 minutes. Santene (2.4 g, 20 mmol) was added slowly dropwise over 30 minutes. After stiffing for 3 hours at ambient temperature the reaction medium was diluted with ethyl acetate then it was added NaHCO₃ and the all was left overnight stirring. The reaction medium was extracted with ethyl acetate, washed with brine, dried over MgSO₄, filtered and the solvents removed in vacuo to yield 8.57 g of crude oil.

Bulb to bulb distillation at 0.55 mbar at 80-100° C. gave light fractions 2.8 g and residue 3.62 g. Further purification of the residue by chromatography (cartridge 120 g) with cyclohexane then 2:98 ethyl acetate:cyclohexane as eluant, gave the enol acetate, 1.21 g, yield=27% identical to that prepared above (exo:endo 4:1 isomers).

Procedure 4: Use of ZnI₂

ZnI₂ (320 mg, 1 mmol) was added to a stirred solution of santene (6.1 g, 50 mmol) and allylidene diacetate (15.8 g, 100 mmol) and the mixture stirred at ambient temperature. Trimethyl silyl chloride (4.9 g, 45 mmol) was added slowly dropwise over 1 hour. After 3 hours stirring at ambient temperature, the medium was diluted with ethyl acetate, then poured into NaHCO₃, stirred vigorously for 10 minutes then extracted with ethyl acetate, and the combined organic phases washed with brine, then dried over MgSO₄, filtered and the solvents removed in vacuo to yield the crude enol acetate. The crude enol acetate, after addition of potassium acetate (2.0 g.), was purified by bulb to bulb distillation first at 1.0 mbar at 80° C. to eliminate lights, then the residue was distillated at 175° C. at 1.2 mbar to gave a first fraction which was purification by chromatography cartridge 200 g with cyclohexane then 98:2 cyclohexane:ethyl acetate to obtain the desired enol acetate 3.5 g, yield=32%, (exo:endo, 4:1 isomers).

Procedure 5: Use of ZnBr₂

ZnBr₂ (1.13 g, 5 mmol, 10 mol %) was added to allylidene diacetate (11.9 g, 75 mmol) at ambient temperature and the suspension vigorously stirred for a further 15 minutes to give a suspension. Santene (6.0 g, 50 mmol) was added via syringe pump over 90 minutes at ambient temperature. The reaction was stirred at ambient temperature for 24 hours. The reaction medium was diluted with ethyl acetate and added NaHCO₃, stirred overnight at ambient temperature. Extracted with ethyl acetate, washed with NaHCO₃, then dried over MgSO₄, filtered and the solvents removed in vacuo to yield the crude enol acetate. The crude enol acetate, after addition of potassium acetate (2.0 g.), was purified by bulb to bulb distillation 0.09 mbar gave 80° C. to eliminate lights, then the residue was distillated at 120-190° C. to gave a first fraction which was re-distilled by bulb to bulb distilled 125° C.-140° C. at 0.09 mbar to obtain the desired enol acetate 2 g, yield=18%. (4:1 mixture of exo:endo isomers).

Procedure 6: Other Catalysts

General Method

The Lewis acid (5-10 mol %) was added to a stirred mixture of santene (122 mg, 1 mmol) and the allylidene diacetate (180 mg, 1.1 mmol) in dichloromethane (1 mL) cooled to 0° C. After 30 minutes at 0° C. the solution were allowed to warm to ambient temperature and stirred for a further 2-4 hours at ambient temperature. Conversion analysed by GC.

| Catalyst 5 mol % | Compound (I) | Ratio exo:endo | Compound (I") |
|---|---|---|---|
| Ce(OTf)₃ | 8 | 50:50 | |
| Cu(OTf)₂ | 5 | 55:45 | |
| FeCl₃ | 5 | 80:20 | |
| Sc(OTf)₂ | 12 | 66:34 | |
| Al(OTf)₃ | 11 | 45:55 | |
| Zn(OAc)₂ + TMS—Cl (0.9 eq) | 17 | 84:16 | 13 |
| BF₃•OEt₂ | 20 | 80:20 | — |

Example 2

Preparation of other (E)-3-((1SR,2RS,4RS)-2-methyl-3-methylenebicyclo[2.2.1]heptan-2-yl)prop-1-en-1-yl carboxylates General Procedure:

ZnI₂ (10 mol %) was added to the suitable allylidene diester (20-200 mmol, 2 equivalents) at ambient temperature. After stirring the suspension for 30 minutes at ambient temperature santene (10-100 mmol, 1 eq) was added slowly dropwise over 15 minutes then the solution was stirred for a further 20-40 hours at ambient temperature then diluted with ethyl acetate and poured into saturated NaHCO₃ solution. The medium was extracted with ethyl acetate, and the combined organic phases washed with NaSO₃ (15%, 100 ml), then water, and then dried over MgSO₄, filtered and the solvents removed in vacuo. The residue was further purified by bulb to bulb or fractional distillation to give the pure enol esters as a mixture of exo and endo isomers. If necessary chromatography was performed over silica gel (20:1 silica to weight of product, Analogix Cartridge), with cyclohexane then 98:2 then 96:4 cyclohexane:ethyl acetate as eluent gave the pure enol ester as a mixture of exo and endo isomers.

(E)-3-((1SR,2RS,4RS)-2-methyl-3-methylenebicyclo[2.2.1]heptan-2-yl)prop-1-en-1-yl propionate Bulb to bulb distillation 95° C. at 0.45 mbar gave a light fraction and residues. The residues was further purified by chromatography (cartridge 80 g) with cyclohexane then 2:98

Ethyl acetate:cyclohexane as eluent gave the pure enol propionate, 0.94 g, yield=40% (4:1 mixture of exo:endo isomers).

$^{13}$C NMR: 171.7 (C), 165.1 (C), 136.6 (CH), 111.5 (CH), 100.2 (CH$_2$), 46.9 (CH), 44.8 (CH), 44.7 (C), 38.6 (CH$_2$), 37.0 (CH$_2$), 29.6 (CH$_2$), 27.3 (CH$_2$), 23.6 (CH$_2$), 22.8 (CH$_3$), 8.8 (CH$_3$)

(E)-3-((1SR,2RS,4RS)-2-methyl-3-methylenebicyclo [2.2.1]heptan-2-yl)prop-1-en-1-yl isobutyrate Bulb to bulb distillation 105° C. at 0.45 mbar gave a light fraction and residue. Further purification of the residue by chromatography (cartridge 80 g) with 2:98 ethyl acetate: cyclohexane as eluent gave desired enol isobutyrate, 1.15 g, yield=46% (4:1 mixture of exo:endo isomers).

$^{13}$C NMR: 174.3 (C), 165.2 (C), 136.8 (CH), 111.5 (CH), 100.2 (CH$_2$), 46.8 (CH), 44.8 (CH), 44.7 (C), 38.6 (CH$_2$), 37.0 (CH$_2$), 33.8 (CH), 29.6 (CH$_2$), 22.8 (CH$_3$), 18.8 (CH$_3$)

(E)-3-((1SR,2RS,4RS)-2-methyl-3-methylenebicyclo [2.2.1]heptan-2-yl)prop-1-en-1-yl pivalate After 24 hours at ambient temperature the mixture was heated at 45° C. for a further 90 minutes then at 60° C. for a further 60 minutes. Added a further portion of ZnI$_2$ (160 mg, 0.5 mmol) continued heating at 60° C. for a further 30 minutes prior to usual workup. Bulb to bulb distillation 0.45 mbar at 110° C. gave lights and residues. Further purification of the residues by chromatography (cartridge 80 g) with cyclohexane then 1:99 EtOAc:cyclohexane as eluent gave the desired enol pivalate, 1.0 g, yield=38% (4:1 mixture of exo:endo isomers).

$^{13}$C NMR: 175.7 (C), 165.2 (C), 137.0 (CH), 111.4 (CH), 100.1 (CH$_2$), 46.8 (CH), 44.8 (C), 44.7 (CH), 38.7 (CH$_2$), 37.0 (CH$_2$), 29.6 (CH$_2$), 27.1 (C), 23.7 (CH$_2$), 22.8 (CH$_3$)

(E)-3-((1SR,2RS,4RS)-2-methyl-3-methylenebicyclo [2.2.1]heptan-2-yl)prop-1-en-1-yl isobutyrate using EtAlCl$_2$ as catalyst Ethyl aluminum dichloride (9.0 ml, 1.0 M in hexanes, 9 mmol) was added slowly dropwise to a stirred solution of santene (1.22 g, 10 mmol) and the allylidene diisobutyrate (2.68 g, 25 mmol) cooled to 0° C. The reaction mixture was stirred at 0° C. for a further 2 hours then allowed to warm to ambient temperature overnight. The mixture was then poured into saturated NaHCO$_3$ solution then extracted twice with diethyl ether, washed the combined organic phase with brine, then dried over anhydrous sodium sulfate, filtered and the solvent removed in vacuo to yield a mixture of the enol isobutyrate and chloro enol isobutyrate (enol ester:chloro, 35:24). Further purification by bulb to bulb distillation 180° C. at 0.1 mbar gave a mixture of the desired enol isobutyrate and of the rearranged chloro compound, 1.22 g (ratio 66:26, exo:endo 6:1), yield=50%. The enol isobutyrate was spectroscopically identical to that prepared previously.

(E)-3-((1SR,2RS,4RS)-2-methyl-3-methylenebicyclo [2.2.1]heptan-2-yl)prop-1-en-1-yl-benzoate using ZnI$_2$ as catalyst ZnI$_2$ (10 mol %, 32 mg, 0.1 mmol) was added in one portion to a stirred solution of prop-2-ene-1,1-diyl dibenzoate (see *J. Am. Chem. Soc.*, 2010, 132, 1760-1761) (290 mg, 1 mmol) and santene (130 mg, 1 mmol) in CH$_2$Cl$_2$ (1 mL) at ambient temperature. The stirring was prolonged overnight at ambient temperature. Diluted with ethyl acetate and NaHCO$_3$, extracted with ethyl acetate, dried organic phase over MgSO$_4$, filtered and the solvents removed in vacuo to yield the crude enol benzoate, 450 mg. Further purification by chromatography with a cartridge (silica, 40 g) with cyclohexane then 2:98 ethyl acetate:cyclohexane as eluent, gave the desired enol benzoate, 110 mg, 39%. (exo:endo, 3:1).

$^{13}$C NMR: 165.1 (C), 163.8 (C), 136.8 (CH), 133.4 (CH), 129.9 (CH), 129.3 (C), 128.5 (CH), 112.3 (CH), 100.3 (CH$_2$), 46.8 (CH), 44.8 (C), 44.8 (CH), 38.7 (CH$_2$), 37.0 (CH$_2$), 29.6, 23.6 (CH$_2$), 22.9 (CH$_3$).

Example 3

Preparation of (E)-3-((1SR,2RS,4RS)-2-methyl-3-methylenebicyclo[2.2.1]heptan-2-yl)prop-1-en-1-yl acetate from a silyl derivative of formula (II)

Preparation of the Silyl Derivative of Formula (II)

Dimethoxy(methyl)(((1SR,4RS)-3-methylbicyclo [2.2.1]hept-2-en-2-yl)methyl)silane Triethyl aluminum (1.0 M in hexanes, 2.5 mL, 2.5 mmol) was added slowly dropwise to a suspension of Ni(acac)$_2$ (dried in vacuo 120° C. 3 hrs, 130 mg, 0.4 mmol, 5 mol %), santadiene (1.2 g, 10 mmol) in freshly degassed toluene (80 mL) cooled to 0° C. After 15 minutes, dimethoxy methyl silane (1.2 mL, 10 mmol) was added slowly dropwise and the solution was then allowed to slowly warm to ambient temperature and stirred for a further 2 hours. The reaction mixture was poured into saturated ammonium chloride solution and extracted with ether, then the combined organic phase was washed with brine and dried over Na$_2$SO$_4$, then filtered and the solvents removed in vacuo to yield the crude allyl silane 1.5 g, which was further purified by bulb to bulb distillation 75° C. at 0.08 mbar and gave the desired allyl silane 1.2 g, 53%.

$^{13}$C NMR: 134.7 (C), 134.3 (C), 50.3, 50.2 (CH$_3$), 47.6 (CH), 47.4 (CH), 46.6 (CH$_2$), 26.0, 25.9 (CH$_2$), 13.5 (CH$_2$), 12.0 (CH$_3$), −5.5 (CH$_3$) ppm.

Coupling:

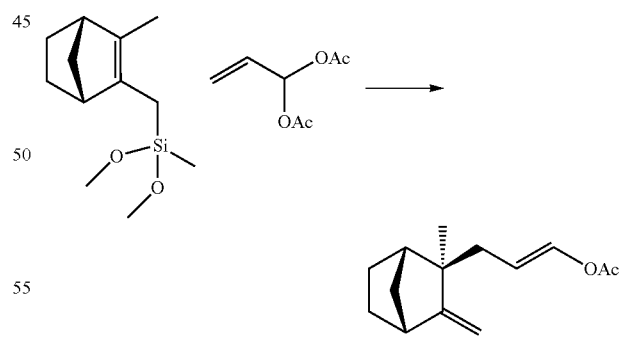

ZnBr$_2$ (10 mol %, 30 mg, 0.13 mmol) was added to a stirred solution of the above silane (225 mg, 1 mmol) and allylidene diacetate (160 mg, 1 mmol) in CH$_2$Cl$_2$ (1 mL) and the suspension stirred at ambient temperature for 15 hours then poured into NaHCO$_3$, extracted with ethyl acetate, washed with brine, dried over MgSO$_4$, filtered and the solvents removed in vacuo to yield the crude enol acetate, 243 mg. (exo:endo) identical to that prepared previously (containing starting diacetate 26% by GC).

Example 4

Synthesis of 3-((1SR,2RS,4RS)-2-methyl-3-methyl-enebicyclo[2.2.1]heptan-2-yl)propanal (Compound (IV))

Procedure 1: Hydrolysis with 4-Dimethylamino Pyridine

The enol acetate (as obtained in Example 1 procedure 4, 11.1 g, 50 mmol) was dissolved in methanol (50 ml) and 4-dimethylamino pyridine (915 mg, 7.5 mmol, 15 mol %) was added then the solution degassed with argon bubbling for 30 minutes and then the solution heated under reflux for 18 hours. The reaction medium was diluted with cyclohexane, and washed with $NH_4Cl$, re-extracted aqueous phase with with cyclohexane, washed with water then dried over $MgSO_4$, filtered and the solvents removed in vacuo to yield the crude aldehyde. Further purification by bulb to bulb distillation gave the desired aldehyde, 7.0 g, yield=78%, as a mixture of isomers exo:endo 75:18.

$^{13}$C NMR: 202.8 (C), 165.0 (C), 100.6 ($CH_2$), 46.8 (CH), 45.0 (CH), 44.1 (C), 40.1 ($CH_2$), 37.0 ($CH_2$), 32.6 ($CH_2$), 29.6 ($CH_2$), 23.6 ($CH_2$), 22.5 ($CH_3$)

Procedure 2: Hydrolysis with Diazabicyclo[2.2.2]Octane

Diazabicyclo[2.2.2]octane (20 mg, cat.) was added to a stirred solution of the enol acetate (as obtained in Example 1 procedure 4, 0.2 g, 1 mmol) in methanol (0.8 g) and the mixture was heated under reflux for 6 hours. Diluted with ethyl acetate and washed with $NH_4Cl$, re extracted aqueous phase with ethyl acetate, then dried organic phase over $MgSO_4$, filtered and the solvents removed in vacuo to yield the aldehyde (exo:endo, 4:1 isomers). Identical to that prepared above.

Example 5

Synthesis of (Z)-2-methyl-5-((1SR,2RS,4RS)-2-methyl-3-methylenebicyclo[2.2.1]heptan-2-yl)pent-2-en-1-ol (β-Santalol)

Enal (E)-2-methyl-5-((1SR,2RS,4RS)-2-methyl-3-methylenebicyclo[2.2.1]heptan-2-yl)pent-2-enal (compound (V))

To a solution of the aldehyde (IV) (7.0 g, 39.3 mmol) in toluene (25 ml) was added a solution of hexamethylene imine benzoate (1.0 M solution, 7.8 ml, 7.8 mmol, 0.2 eq) and the suspension heated to 85° C. Propanal (4.6 g, 80 mmol) was then added over 30 minutes. The solution was heated for an additional 30 minutes then cooled. Then the reaction medium was washed with $NH_4Cl$, an the aqueous phase reextracted with ethyl acetate, and the combined organic phases where washed with $NaHCO_3$, then dried over $MgSO_4$, filtered and the solvents removed in vacuo to yield the crude enal. Further purification by bulb to bulb distillation 1.0 mbar at 100-150° C. gave impurities, then the enal, 6.7 g, yield=78%, (exo:endo 4:1 isomers).

$^{13}$C NMR: 195.2 (C), 165.5 (C), 155.2 (CH), 139.1 (C), 100.3 ($CH_2$), 46.8 (CH), 44.8 (CH), 44.7 (C), 39.4 ($CH_2$), 37.1 ($CH_2$), 29.6 ($CH_2$), 24.9 ($CH_2$), 23.7 ($CH_2$), 22.6 ($CH_3$), 9.1 ($CH_3$)

(1E,3E)-2-methyl-5-((1SR,2RS,4RS)-2-methyl-3-methylenebicyclo[2.2.1]heptan-2-yl)penta-1,3-dien-1-yl propionate (compound (VI))

Propionic anhydride (7.15 g, 55 mmol) and then triethylamine (2.72 g, 27 mmol) and potassium propionate (0.2 g, cat.) were added to the enal (V) (5.87 g, 27 mmol) the suspension was degassed with argon for 15 minutes then heated under an argon atmosphere at 70° C. for 42 hours. The reaction was then cooled and diluted with ethyl acetate and poured into $NaHCO_3$ then stirred overnight. The aqueous phase re-extracted with ethyl acetate, then dried combined organic phase over $MgSO_4$, then filtered and the solvents removed in vacuo to yield the crude propionate. Further purification by chromatography (cartridge 200 g) with cyclohexane then 1:99 ethyl acetate:cyclohexane as eluent gave the desired enol propionate, 5.6 g, yield=76%. Further purification by bulb to bulb distillation 150° C. at 0.45 mbar gave the dienol propionate 4.45 g, (exo:endo 4:1 isomers and (E,E):(E,Z), 4:1).

$^{13}$C NMR: 171.3 (C), 165.5 (C), 134.4 (CH), 130.7 (CH), 126.7 (CH), 120.6 (C), 100.0 ($CH_2$), 46.9 (CH), 45.3 (C), 45.0 (CH), 44.5 ($CH_2$), 37.0 ($CH_2$), 29.7 ($CH_2$), 27.5 ($CH_2$), 23.6 ($CH_2$), 23.0 ($CH_3$), 10.4 ($CH_3$), 9.0 ($CH_3$)

(Z)-2-methyl-5-((1SR,2RS,4RS)-2-methyl-3-methylenebicyclo[2.2.1]heptan-2-yl)pent-2-en-1-yl propionate (compound (VII))

The freshly distilled dienyl propionate (VI) (4.35 g, 15.8 mmol) and maleic acid (112 mg) were placed in a s/s autoclave and the catalyst RuCp*(COD)$BF_4$, (45 mg, 1 mol %) was then added. Acetone (10 ml, degassed with ultrasound and argon bubbling, stored under argon) was added last and the mixture sealed and evacuated then purged with hydrogen 5 times. The suspension was stirred under an atmosphere of hydrogen 5 bars at 60° C. for 3 hours. Then filtered through a plug of silica (5 cm) with ethyl acetate as eluent then the solvents removed in vacuo to yield the crude propionate, 4.5 g. Further purification by column chromatography (cartridge 200 g) with 1:99 ethyl acetate:cyclohexane as eluent gave the pure propionate, 2.73 g plus mixed fractions, 1.23 g (containing unreacted E,Z isomer) (total 3.96 g, 90%). The pure fraction (2.73 g) was further purified by bulb to bulb distillation 175° C. at 6.0×10$^{-1}$ mbar to give the pure (Z)-propionate, 2.63 g as a mixture of exo:endo, 4,1, (Z:E selectivity >98:2).

$^{13}$C NMR: 174.5 (C), 166.2 (C), 131.2 (CH), 129.6 (C), 99.7 ($CH_2$), 63.0 ($CH_2$), 46.8 (CH); 45.1 (C), 44.6 (CH), 41.2 ($CH_2$), 37.1 ($CH_2$), 29.7 ($CH_2$), 27.6 ($CH_2$), 23.7 ($CH_2$), 23.4 ($CH_2$); 22.6 ($CH_3$), 21.4 ($CH_3$), 9.2 ($CH_3$)

(Z)-2-methyl-5-((1SR,2RS,4RS)-2-methyl-3-methylenebicyclo[2.2.1]heptan-2-yl)pent-2-en-1-ol (β-Santalol)

The propionate obtained above (2.53 g, 9 mmol) was dissolved in methanol (20 ml) and $K_2CO_3$ (1.85 g 13.4 mmol) was added and the solution was stirred for 3 hours. The majority of the methanol was removed in vacuo then the residue was portioned between cyclohexane and water. The aqueous phase was re-extracted with cyclohexane and then the combined organic phases washed with water, then $NaHCO_3$, dried over $K_2CO_3$ and $MgSO_4$, then filtered. The solvents were removed in vacuo to yield the crude β-santalol, 2.01 g. Further purification by bulb to bulb distillation 155° C. at 0.78 mbar gave a mixture of epi-β-santalol and β-santalol (i.e. endo:exo) 1:4., 1.85 g 92% (Z:E selectivity >98:2).

$^{13}$C NMR: 166.2 (C), 133.9 (C), 129.0 (CH), 99.7 ($CH_2$), 61.6 ($CH_2$), 46.8 (CH), 44.7 (C), 44.6 (CH), 41.5 ($CH_2$), 37.1 ($CH_2$), 29.7 ($CH_2$), 23.7 ($CH_2$), 23.2 ($CH_2$), 22.6 ($CH_3$), 21.3 ($CH_3$)

What is claimed is:

1. A compound of formula

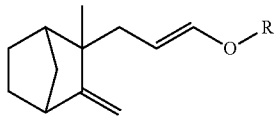
(I)

in the form of any one of its stereoisomers or mixtures thereof, and wherein R represents a group of formula $COR^a$ having between 2 and 10 carbon atoms, wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms.

2. A compound according to claim 1, wherein R is a $C_{3-7}$ acyl group.

3. A process for the preparation of a compound of formula

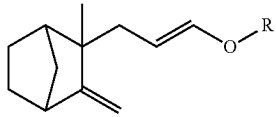
(I)

in the form of any one of its stereoisomers or mixtures thereof, and wherein R represents a group of formula $COR^a$ having between 2 and 10 carbon atoms, wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms;
by reacting together a compound of formula

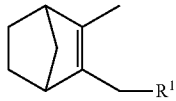
(II)

in the form of any one of its stereoisomers or mixtures thereof, and wherein $R^1$ represents a hydrogen atom or a $Si(R^2)_3$ or $B(OR^{2'})_2$ group, $R^2$ representing a $C_{1-4}$ alkyl or alkoxyl group and $R^{2'}$ representing, taken separately, a $C_{1-4}$ alkyl group or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups;
with a compound of formula

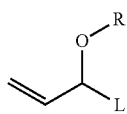
(III)

in the form of any one of its stereoisomers or mixtures thereof, and wherein R has the meaning defined in formula (I) and L represents a halogen atom or an OR group;
in the presence of
1) at least one Lewis acid selected amongst
   i) a metal salt selected from the group consisting of an element of the group 2, 3, 4, 13 of the Periodic Table, a 3d element having an atomic number of 21 to 30, and tin;
   ii) an alkyl aluminium chloride of formula $Al(R^4)_a Cl_{3-a}$, a representing 1 or 2 and $R^4$ representing $C_{1-10}$ alkyl or alkoxide group; and
   iii) a boron derivative of formula $BZ_3$, wherein Z represents a fluoride or a phenyl group optionally substituted by one or two methyl groups, and any one of its adducts with a $C_2$-$C_{10}$ ether or a $C_1$-$C_8$ carboxylic acid; and
2) optionally an additive selected amongst the group consisting of alkaline-earth hydroxide or oxide and of the compounds of formula $R^b COCl$, $ClSi(R^b)_3$, $R^b COOR^c$ or $(R^b COO)_2 R^d$, $R^b$ representing a $C_{1-12}$ alkyl group or a phenyl group optionally substituted by one or two $C_{1-4}$ alkyl or alkoxyl groups, and $R^c$ representing a alkaline metal cation or a $R^b CO$ acyl group, and Rd representing a alkaline-earth metal cation.

4. A process according to claim 3, wherein $R^1$ is a hydrogen atom.

5. A process according to claim 3, wherein R is a $C_{2-5}$ acyl group.

6. A process according to claim 3, wherein the metal salt is selected amongst a salt of formula

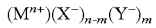

wherein m is an integer from 0 to (n−1), and
n is 2 and M is Zn, Cu or an alkaline earth metal;
n is 3 and M is a lanthanide, Sc, Fe, Al; or
n is 4 and M is Sn, Ti or Zr;
each $X^-$ represents $Cl^-$, $Br^-$, $I^-$, a weakly-coordinating monoanion, $R^3 SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups;
each $Y^-$ represents a $C_{1-6}$ carboxylate or 1,3-diketonate when n is 2 or 3, or a $C_{1-6}$ alkoxylate when n is 3 or 4.

7. A process according to claim 3, wherein the metal salt is selected amongst a salt of formula

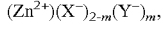

wherein m is an integer from 0 to 1;

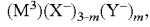

wherein M is Al or Sc and m is an integer from 0 to 2:

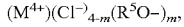

M representing Ti or Zr, and $R^5$ representing $C_{1-3}$ alkyl group and m is an integer from 0 to 3;
and wherein each $X^-$ represents $Cl^-$, $Br^-$, $I^-$, a weakly-coordinating monoanion, $R^3 SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups;
each $Y^-$ represents a $C_{1-6}$ carboxylate or 1,3-diketonate when n is 2 or 3, or a $C_{1-6}$ alkoxylate when n is 3 or 4.

8. A process according to claim 3, wherein $Y^-$ represents a $C_{1-6}$ carboxylate when n is 2 or 3, or a $C_{1-3}$ alkoxylate when n is 4.

9. A process according to claim 3, wherein said alkyl aluminium chloride is selected amongst the compounds of formula $Al(R^4)_a Cl_{3-a}$, a representing 1 or 2 and $R^4$ representing a $C_{1-3}$ alkyl group.

10. A process according to claim 3, wherein said boron derivative is $BF^3$ or an adduct of $BF^3$ with either a $C_4$-$C_6$ ether or a $C_1$-$C_3$ carboxylic acid.

11. A process according to claim 3, wherein said additives are $ClSiMe_3$, MeCOCl, AcOK or AcOAc.

12. A compound of formula

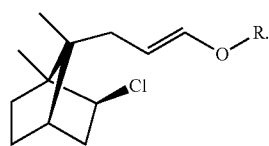

(I″)

in the form of any one of its stereoisomers or mixture thereof, and wherein R has the same meaning defined in claim 1.

* * * * *

UNITED STATES PATENT AND TRADEMARK OFFICE
CERTIFICATE OF CORRECTION

PATENT NO. : 9,056,826 B2
APPLICATION NO. : 14/130921
DATED : June 16, 2015
INVENTOR(S) : Birkbeck Page 1 of 1

It is certified that error appears in the above-identified patent and that said Letters Patent is hereby corrected as shown below:

In the Claims

Column 19:
Line 52, after "or alkoxyl group and", delete "$R^2$" and insert -- $R^{2'}$ --.

Column 20:
Line 25, after "metal cation or a $R^bCO$ acyl group, and", delete "Rd" and insert -- $R^d$ --.
Line 52, delete the formula "$(M^3)(X^-)_{3-m}(Y^-)_m$," and insert -- $(M^{3+})(X^-)_{3-m}(Y^-)_m$, --.
Line 55, delete the formula "$(M^{4+})(Cl^{-)})_{4-m}(R^5O-)_m$," and insert -- $(M^{4+})(Cl^-)_{4-m}(R^5O^-)_m$, --.

Column 21:
Line 6, delete both occurrences of "$BF^3$" and insert -- $BF_3$ --.

Signed and Sealed this
Sixth Day of October, 2015

Michelle K. Lee
*Director of the United States Patent and Trademark Office*